United States Patent

Nagase

[11] 4,328,367
[45] May 4, 1982

[54] TETRAHYDROPHTHALAMIDE DERIVATIVES

[75] Inventor: Hiroshi Nagase, Kawanishi, Japan

[73] Assignee: Takeda Chemical Industries, Ltd., Osaka, Japan

[21] Appl. No.: 963,762

[22] Filed: Nov. 27, 1978

[30] Foreign Application Priority Data

Nov. 29, 1977 [JP] Japan ............................... 52-143672
Oct. 27, 1978 [JP] Japan ............................... 53-133015

[51] Int. Cl.³ ...................... C07C 102/08; A01N 7/02
[52] U.S. Cl. ...................................... 564/155; 71/88; 71/98; 71/103; 71/105; 71/106; 71/107; 71/113; 71/115; 71/118; 564/154; 564/158; 549/480; 549/481; 549/482; 549/493
[58] Field of Search ............... 260/557, 347.3; 71/118, 71/88, 107, 98, 113, 103, 115, 105, 106; 564/154, 155, 158

[56] References Cited

U.S. PATENT DOCUMENTS 3,980,662 9/1976 Watanabe et al. ............ 260/557 R

FOREIGN PATENT DOCUMENTS 48-96722 10/1973 Japan .

*Primary Examiner*—Mary C. Lee
*Assistant Examiner*—James H. Turnipseed
*Attorney, Agent, or Firm*—Burgess, Ryan and Wayne

[57] ABSTRACT

Novel tetrahydrophthalamide derivatives of the general formula:

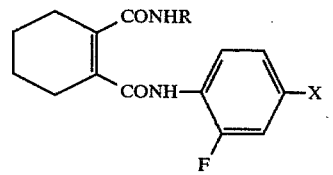

wherein X is chlorine or bromine, and R is hydrogen, or an alkyl, a substituted alkyl, a cycloalkyl, a substituted cycloalkyl, an alkenyl, or an alkynyl group, have strong herbicidal activity and are particularly, useful for selectively controlling weeds without causing any substantial injury to soybean and other crop plants.

13 Claims, No Drawings

TETRAHYDROPHTHALAMIDE DERIVATIVES

This invention relates to novel tetrahydrophthalamide derivatives of the general formula:

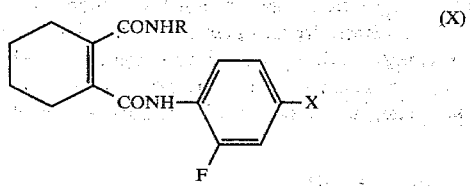

wherein X is chlorine or bromine, and R is hydrogen or an alkyl, a substituted alkyl, a cycloalkyl, a substituted cycloalkyl, an alkenyl or an alkynyl group, which have herbicidal activity, to methods of producing the same and preparations containing the same.

The research undertaken by me in search for herbicides led to the finding that the new compounds (I) mentioned above display excellent herbicidal activity against grasses and broadleaf weeds. The compounds (I) are highly effective against annual and perennial grasses or weeds and can be used as herbicides effectively in the paddy-fields or/and upland crop lands. Grasses and weeds sensitive to these compound (I) are: in paddy fields annual monocotyledonous plants such as barnyard grass *Echinochloa oryzicola* Vasing., umbrella plant *Cyperus difformis* L., monochoria *Monochoria vaginalis* PRESL., etc., annual dicotyledonous plants such as false pimpernel *Lindernia procumbens* Philcox, toothcup *Rotala indica* KOEHNE, etc. and perennial weeds such as spike rush *Eleocharis acicularis* Roem, et Schult., *Sagittaria pygmaea* Miq., *Cyperus serotinus* Rottb., *Scirpus juncoides* Roxb. var. *ohwianus* J. Koyama, etc. and in upland crop lands, annual monocotyledonous plants such as crabgrass *Digitaria adscendens* HENR., *Setaria viridis* Beauv, *Echinochloa crus-galli* Beauv. var. *praticola* Ohwi, *Panicum dichotomiflorum* Michx., *Commelina communis* L., water fox tail *Alopeculus aqualis* Sobol. var. *amurensis* Ohwi, annual blue grass *Poa annua* L., etc and annual dicotyledonous plants such as common chickweed *Stellaria media* Vill., pig weeds *Amaranthus retroflexus* L., lamb's quarters *Chenopodium album* L., inutade *Polygonum Blumei* Meisn. and common purslane *Portulaca oleracea* L., *Sida spinosa* L., *Abutilon theophrasti* Medic., *Xanthium strumarium* L. and perennial weeds such as *Sorghum halpense* Pers. The compounds (I) can be applied both in the pre-emergence and in post-emergence states. In view of the high selectivity of compounds (I) when applied in a pre-emergence treatment to crop plants, particularly to leguminous plants, these compounds (I) are able to selectively control the aforementioned weeds without causing any substantial injury to soybean and other crop plants. These findings were followed by further research which has culminated in the completion of this invention.

Referring to R in general formula (I), the alkyl group is a straight-chain or branched alkyl group such as methyl, ethyl, propyl, isopropyl, butyl, isobutyl, sec.-butyl, tert.-butyl, pentyl, isopentyl, hexyl, heptyl, octyl, nonyl, decyl, lauryl or stearyl, alkyls containing 1 to 10 carbon atoms being particularly preferred.

As examples of the substituted alkyl group, there may be mentioned alkyl groups which are substituted, for example by hydroxyl, cyano, halogen (e.g. chlorine, bromine, etc.), carboxyl, straight-chain or branched alkoxy groups of 1 to 8 carbon atoms (e.g. methoxy, ethoxy, isopropoxy, n-propoxy, etc.), alkoxycarbonyl groups of 1 to 4 carbon atoms (e.g. ethoxycarbonyl, etc.), acyloxy groups of 1 to 10 carbon atoms (e.g. acetoxy, propionyloxy, benzoyloxy, etc.), furyl which may optionally be substituted, for example by nitro, halogen or lower alkyl of 1 to 3 carbon atoms, groups represented by the general formula:

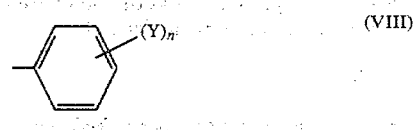

[wherein Y is hydrogen, halogen, lower alkyl, lower alkoxy, nitro or hydroxyl; n is an integer of 1, 2 or 3], or groups represented by the general formula:

[wherein $R^1$ is a straight-chain or branched alkyl group of 1 to 5 carbon atoms; m is an integer of 0, 1 or 2]

In the formula (VIII), the halogen is preferably chlorine or bromine, the lower alkyl is preferably an alkyl group of 1 to 3 carbon atoms and the lower alkoxy is preferably an alkoxy group of 1 to 3 carbon atoms. The group (VIII) is preferably an unsubstituted phenyl group or a phenyl group substituted by one or two substituents such as chlorine or methyl. As preferred examples of the group (IX), there may be mentioned ethylthio, n-propylthio, n-butylthio, ethylsulfinyl, ethylsulfonyl, n-propylsulfinyl, n-propylsulfonyl and n-butylsulfonyl.

Especially desirable substituted alkyls are such that the alkyl moiety thereof is a straight-chain alkyl group of 1 to 4 carbon atoms. The substituted alkyl may have two or more substituents which may be the same substituent group of different groups.

As examples of said cycloalkyl group, there may be mentioned alkyls of 3 to 8 carbon atoms, preferably of 3 to 6 carbon atoms, such as cyclopropyl, cyclobutyl, cyclopentyl or cyclohexyl. As examples of the substituted cycloalkyl group, there may be mentioned said cycloalkyl groups which are substituted, for example by lower alkyl groups having 1 to 4 carbon atoms or halogen (e.g. chlorine, bromine, etc.). The alkenyl group is an alkenyl containing 2 to 8 carbon atoms, preferably 3 to 6 carbon atoms, such as allyl, methallyl, pentenyl, butenyl or hexenyl. The alkynyl group is an alkynyl containing 2 to 8 carbon atoms, preferably 3 to 6 carbon atoms, such as propargyl. These alkenyls or alkynyls may be optionally substituted, for example, by a phenyl group.

Compounds of formula (I) can be produced, for example by reacting a tetrahydroisophthalimide compound of the general formula:

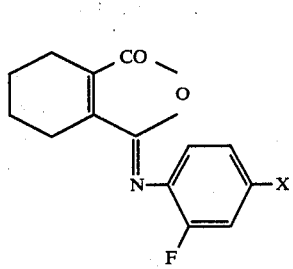

wherein the symbol X is as defined hereinbefore, with a compound of the general formula:

R—NH$_2$ (III)

wherein R is as defined hereinbefore.

In case the compound (III) is a primary amine, this may be employed either as the free base or in the form of a salt which does not affect the reaction. As examples of a salt of the primary amine (III), there may be mentioned the salts with hydrogen halides, e.g. hydrogen chloride, hydrogen bromide, etc. and with inorganic or organic acids such as sulfonic acid, nitric acid, oxalic acid, acetic acid and so forth. In case the compound (III) is ammonia, it may be employed in a gaseous state or in a solution of a suitable solvent. The reaction is normally carried out using about 1 to several moles, preferably about 1 to 1.2 moles, of the compound (III) to each mole of compound (II). The reaction is desirably conducted in an inert solvent such as a hydrocarbon (e.g. benzene, toluene, hexane, cyclohexane, etc.), a halogenated hydrocarbon (e.g. dichloromethane, carbon tetrachloride, chlorobenzene, etc.), diethyl ether, dioxane, tetrahydrofuran, acetonitrile, acetone, methyl ethyl ketone, ethyl acetate, nitrobenzene or the like. The reaction is normally conducted at about 5° C. to about 60° C. and preferably between 20° C. and 40° C. Normally, the reaction time is about 5 minutes to about 10 hours and, desirably, 10 minutes to one hour.

The compound (I) thus obtained can be isolated and purified by conventional procedures, such as concentration, concentration under reduced pressure, extraction with a solvent, phasic transfer, crystallization, recrystallization and chromatography.

The tetrahydrophthalamide derivative (I) can also be produced by reacting a tetrahydroisophthalimide compound of the general formula:

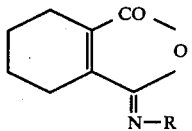 (IV)

wherein R is as defined hereinbefore, with an amine of the general formula:

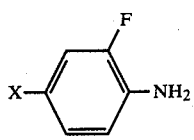 (V)

wherein X is as defined hereinbefore.

The amine (V) may be employed as the free base or in the form of a salt such as those mentioned in connection with (III). Generally this reaction may be conducted under the conditions set forth in connection with the reaction of compound (II) with the compound (III). Thus, the proportions of reactions, solvent, temperature, time, isolation procedures and other parameters may be selected from among those mentioned.

The tetrahydrophthalamide derivative (I) may also be synthesized by the following method which comprises reacting a tetrahydrophthalamic acid directly with a primary amine with the elimination of water:

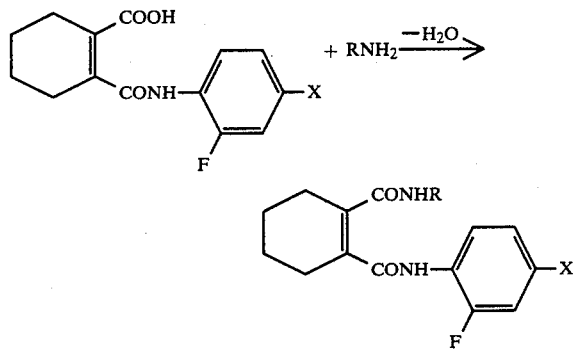

wherein the symbols are as previously defined, or by the following method which comprises reacting a tetrahydrophthalamic acid ester with a primary amine:

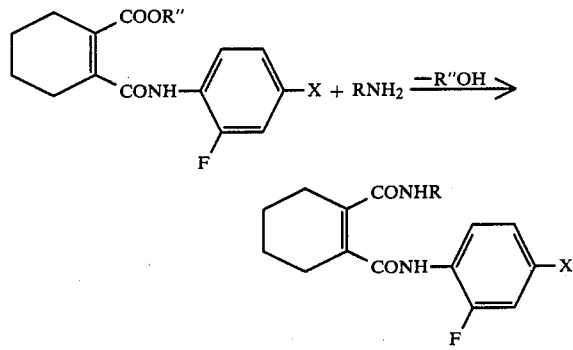

wherein X and R are as previously defined; and R'' is a hydrocarbon residue different from R.

Tetrahydrophthalamide derivatives (I) wherein R is alkylsulfinylalkyl or alkylsulfonylalkyl can also be synthesized by subjecting tetrahydrophthalamide derivatives (I) having an alkylthioalkyl group as the symbol R in the formula (I) to oxidation with, for example, m-chloroperbenzoic acid or hydrogen peroxide. Tetrahydrophthalamide derivatives (I) wherein R is acyloxyalkyl can also be synthesized by subjecting tetrahydrophthalamide derivatives (I) having a hydroxyalkyl group as the symbol R in the formula (I) to acylation with a suitable acylating agent, for example, acetyl chloride.

N-(2-fluoro-4-chlorophenyl)-3,4,5,6-tetrahydroisophthalimide, which falls within the scope of starting material (II) for the purposes of this invention, has been disclosed in U.S. Pat. No. 3,990,880, and other compounds of general formula (II) and compounds of general formula (IV) can be produced, for example by the method described in the above-mentioned patent, a method analogous thereto or a method which may be schematically shown as follows:

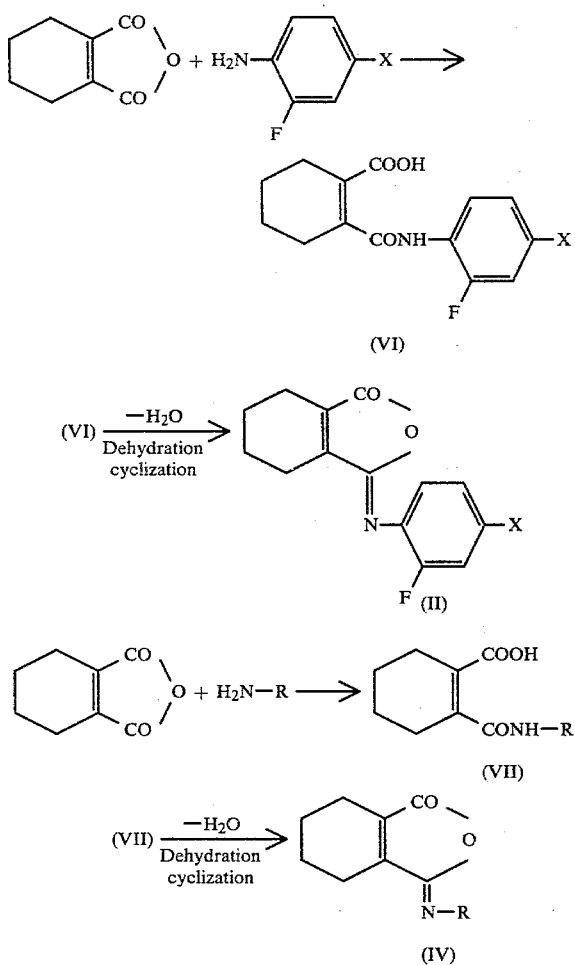

In the above formulae, X and R are as previously defined.

The tetrahydrophthalamic acids (VI) and (VII) can be produced by the processes schematically shown above, i.e. by reacting 3,4,5,6-tetrahydrophthalic anhydride with an amine in substantially equimolar proportions in an inert solvent, normally at 10° to 90° C. and preferably at 20° to 60° C., for 5 minutes to one hour. As examples of said inert solvent there may be mentioned benzene, toluene, hexane, dichloromethane, carbon tetrachloride, chlorobenzene, diethyl ether, dioxane, tetrahydrofuran, acetonitrile, acetone, methyl ethyl ketone, ethyl acetate and nitrobenzene. While both compounds (VI) and (VII) may be isolated and purified by procedures known per se, they may be directly subjected to dehydrative cyclization into compounds (II) and (IV), respectively, with the advantage that isolation and purification procedures are avoided. The dehydrative cyclization of 3,4,5,6-tetrahydrophthalamic acid (VI) or (VII) is advantageously conducted in an inert solvent using a dehydrative-condensing agent. As examples of said dehydrative-condensing agent there may be mentioned carbodiimides such as dicyclohexylcarbodiimide, diethylcarbodiimide, etc., combinations of bases with acylating agents and combinations of bases with acid halide-forming agents. As examples of said bases there may be mentioned tertiary organic amines such as pyridine, quinoline, dimethylaniline, triethylamine, trimethylamine, etc. and alkali metal carbonates and bicarbonates such as sodium carbonate, sodium hydrogen carbonate, potassium carbonate, etc. As examples of said acylating agent there may be mentioned chlorocarbonic acid esters (e.g. methyl chlorocarbonate, ethyl chlorocarbonate, etc.) and benzoyl chloride, while said acid halide-forming agents may for example be phosgene, thionyl halide (e.g. thionyl chloride, thionyl bromide, etc.) and phosphorus oxychloride. The proportion of said dehydrative-condensing agent is normally about 1 to 2 moles and preferably about 1 to 1.2 moles based on each mole of compound (VI) or (VII). When a carbodiimide derivative is used as said dehydrative-condensing agent, the reaction is normally conducted at about 0° C. to about 50° C. With a combination of a base with an acylating agent or an acid halide-forming agent, the reaction is normally carried out at about $-15°$ C. to about 60° C. The reaction time is normally in the range of about 30 minutes to about 3 hours. The inert solvent employed in this dehydrative-cyclization reaction may for example be a hydrocarbon (e.g. benzene, toluene, hexane, cyclohexane, etc.), a halogenated hydrocarbon (e.g. dichloromethane, carbon tetrachloride, chlorobenzene, etc.), diethyl ether, dioxane, tetrahydrofuran, acetonitrile, acetone, methyl ethyl ketone, ethyl acetate or nitrobenzene.

While compounds (II) and (IV) may be isolated and purified by procedures known per se, they may each be directly reacted with said amine to obtain the compound (I) with the advantage that the isolation and purification procedures are avoided.

The compound of this invention (I) may be used for weed control purposes, as follows. One or two or more compounds of general formula (I) are first dissolved or dispersed in a liquid carrier (e.g. a solvent) suited for the intended application or admixed with an appropriate solid carrier (e.g. a diluent or vehicle) or adsorbed thereon and, with the addition of an emulsifier, suspending agent, extender, penetrant, wetting agent, viscosity builder, stabilizer or/and other additives if necessary, are formulated into such application forms as an oil solution, emulsifiable concentrate, wettable powder, dust, granules, tablets, aerosol mist or ointment. These preparations can be produced by conventional procedures.

While the concentration of the active component compound or compounds in such a herbicidal composition varies with the intended application, it is suitable to employ about 10 to 90 weight percent in the case of emulsifiable concentrates or wettable powders, for instance; about 0.1 to 10 weight percent in the case of oil solutions and dusts; and about 1 to 20 weight percent in the case of granules. It should, however, be understood that deviations from the above-indicated range are permissible depending upon the intended application. In using the emulsifiable concentrates and wettable powders, these preparations are advantageously applied as diluted with a diluent such as water to a suitable concentration (e.g. 100 to 100000-fold).

As examples of the aforesaid liquid carrier (solvent) for use in the preparation of the present herbicidal compositions, there may be mentioned water, alcohols (e.g. methanol, ethanol, ethylene glycol, etc.), ketones (e.g. acetone, methyl ethyl ketone, etc.), ethers (e.g. dioxane, tetrahydrofuran, cellosolve, etc.), aliphatic hydrocarbons (e.g. gasoline, kerosene, fuel oil, machine oil, etc.), aromatic hydrocarbons (e.g. benzene, toluene, xylene, solvent naphtha, methylnaphthalene, etc.), halogenated hydrocarbons (e.g. chloroform, carbon tetrachloride, etc.), acid amides (e.g. dimethylformamide, etc.), esters (e.g. ethyl acetate, butyl acetate, fatty acid glycerol esters, etc.), nitriles (e.g. acetonitrile, etc.) and other solvents. These solvents are used alone or as a mixture. The solid carrier (diluent or volume-builder) may for example be any or a mixture of such carriers as vegetable powders (e.g. soybean meal, tobacco leaf powder, wheat flour, saw dust, etc.), mineral powders (e.g. kaolin, bentonite, acid clay and other clays; talc powder, agalmatolite and other varieties of talc; diatomaceous earth, mica powder and other forms of silica), alumina, flowers of sulfur, activated carbon and so on. These solid carriers may be employed alone or as an optional mixture.

As bases for said ointment there may be employed, among others, polyethylene glycol, pectin, polyhydric alcohol esters of higher fatty acids (e.g. glyceryl monostearate), cellulose derivatives (e.g. methyl-cellulose), sodium alginate, bentonite, higher alcohols (e.g. glycerol and other polyhydric alcohols), vaseline, petrolatum album, liquid paraffin, lard, vegetable oils, lanolin, dehydrated lanolin, hydrogenated oil, waxes, resins and so forth. These ointment bases may be employed alone or as a mixture, with or without the addition of surfactants or other additives.

As the surfactants used as emulsifiers, extenders, penetrants, dispersing agents, etc., there may be mentioned soaps, polyoxyalkylaryl esters (e.g. Nonal ®, Takemoto Yushi K.K.), alkylsulfates (e.g. Emal 10 ®, Emal 40 ®, Kao Atlas K.K.), alkylsulfonates (e.g. Neogen ®, Neogen T ®, Daiichi Kogyo Seiyaku K.K., Neopelex ®, Kao Atlas K.K.) polyethylene glycol ethers (e.g. Nonipol 85 ®, Nonipol 100 ®, Nonipol 160 ®, Sanyo Kasei K.K.), polyhydric alcohol esters (e.g. Tween 20 ®, Tween 80 ®, Kao Atlas K.K.) and so on.

For use as a herbicide, the compound (I) is applied in the amount of about 1 to about 50 g, preferably about 2 to about 40 g, per are of a paddy-rice field or about 1 to about 50 g, preferably about 2 to about 40 g, per are of a dry field. Preferably the compound (I) is used as a pre-emergence herbicide. The compound (I) is low in toxicity to mammalian animals and fishes, thus being suited for use in agricultural applications. In herbicidal compositions containing the compound (I) there may be further incorporated other herbicides, plant growth regulators, fungicides (e.g. organochlorine fungicides, organosulfur fungicides, antibiotics, etc.), insecticides (e.g organophosphorus insecticides, natural insecticides, etc.), miticides, nematocides, synergists, attractants, repellents, pigments, fertilizers and so on.

Some exemplary procedures for the production of compounds (II), (IV), (VI) and (VII) will hereinafter be described by way of reference examples.

REFERENCE EXAMPLE 1

(1) Production of 2-fluoro-4-chloroaniline

In benzene, 2-fluoroaniline was acetylated with acetic anhydride to obtain 2-fluoroacetanilide. This 2-fluoroacetanilide was held in glacial acetic acid at 43°–52° C. and an equivalent of chlorine gas was introduced, whereby 2-fluoro-4-chloroacetanilide was obtained. This product was deacetylated with hydrochloric acid and neutralized with sodium hydroxide to recover 2-fluoro-4-chloroaniline as an oil boiling at 64°–65° C./0.25 mmHg.

(2) Process for the production of N-(2-fluoro-4-chlorophenyl)-3,4,5,6-tetrahydrophthalamic acid 3,4,5,6-tetrahydrophthalic anhydride (7.7 g) and 2-fluoro-4-chloroaniline (7.2 g) were added to acetone (50 ml) and, after stirring at 50°–55° C. for 5 minutes, the reaction mixture was concentrated under reduced pressure. The resultant crystals were washed with n-hexane. Yield 13.2 g; m.p. 92°–94° C.

REFERENCE EXAMPLE 2

Process for the production of N-(2-fluoro-4-chlorophenyl)-3,4,5,6-tetrahydroisophthalimide In benzene (40 ml) was suspended N-(2-fluoro-4-chlorophenyl)-3,4,5,6-tetrahydrophthalamic acid (5.0 g) and, following the addition of dicyclohexylcarbodiimide (3.6 g), the suspension was stirred at room temperature for one hour. After the insolubles were filtered off, the filtrate was concentrated to dryness under reduced pressure. The resultant crystals were washed with a small quantity of n-hexane. Yield 3.4 g; m.p. 76°–80° C. As recrystallized from a small quantity of ether, m.p. 82°–84° C.

REFERENCE EXAMPLE 3

(1) Production of 2-fluoro-4-bromoaniline

In methylene chloride (200 ml) was dissolved 2-fluoroaniline (51.0 g) and, under cooling at 0° C. and stirring N-bromosuccinimide (81.7 g) was added in small installments over a period of an hour. The mixture was further stirred for 20 minutes, after which it was washed with cold water and dried over anhydrous sodium sulfate. The methylene chloride layer was concentrated and the resultant oil was distilled under reduced pressure. By the above procedure, there was obtained 2-fluoro-4-bromoaniline as an oil boiling at 75°–80° C./0.3 mmHg.

(2) Production of N-(2-fluoro-4-bromophenyl)-3,4,5,6-tetrahydrophthalamic acid 3,4,5,6-tetrahydrophthalic anhydride (16.0 g) and 2-fluoro-4-bromoaniline (20.0 g) were added to acetone (100 ml) and, after stirring at 40°–45° C. for 2 hours, the mixture was concentrated to dryness under reduced pressure. The resultant crystals were washed with n-hexane. Yield 30.3 g.; m.p. 98°–99° C.

REFERENCE EXAMPLE 4

Production of N-(2-fluoro-4-bromophenyl)-3,4,5,6-tetrahydroisophthalimide

N-(2-fluoro-4-bromophenyl)-3,4,5,6-tetrahydroisophthalamic acid (84.4 g) and dicyclohexylcarbodiimide (51.0 g) were added to toluene (600 ml) and the mixture was stirred at 0°–10° C. for 2 hours. The precipitate was removed and the filtrate was concentrated to dryness under reduced pressure. The oil was washed with n-hexane by decanting. The crystals were recovered by filtration and washed with a small quantity of cold n-hexane. Yield 36.4 g.; m.p. 45°–46° C.

REFERENCE EXAMPLE 5

Production of N-(2-fluoro-4-chlorophenyl)-3,4,5,6-tetrahydroisophthalimide

In benzene (30 ml) was suspended N-(2-fluoro-4-chlorophenyl)-3,4,5,6-tetrahydrophthalamic acid (3.0 g) and, following addition of pyridine (1.6 g) and while the suspension was maintained at 5°–10° C., a solution of thionyl chloride (1.3 g) in benzene (5 ml) was added dropwise over a period of 15 minutes. The reaction mixture was stirred at that temperature for one hour, after which it was thoroughly washed with water and dried over anhydrous sodium sulfate. The benzene layer was concentrated under reduced pressure and, with the addition of a small quantity of n-hexane, the resultant oil was stored in a refrigerator. The crystals separating out were recovered by filtration and washed with a small quantity of cold n-hexane. Yield 2.5 g; m.p. 77°–82° C. As recrystallized from a small quantity of n-hexane, m.p. 82°–84° C.

The following compounds were obtained by the reactions carried out as described in Reference Examples 1 to 3.
(1) N-Isopropyl-3,4,5,6-tetrahydroisophthalimide m.p. 45°–47° C.
(2) N-tert.-Butyl-3,4,5,6-tetrahydroisophthalimide m.p. 70°–73° C.
(3) N-Lauryl-3,4,5,6-tetrahydroisophthalimide m.p. 28°–29° C.
(4) N-Benzyl-3,4,5,6-tetrahydroisophthalimide m.p. 93°–94° C.

EXAMPLE 1

Production of N-isopropyl-N'-(2-fluoro-4-chlorophenyl)-3,4,5,6-tetrahydrophthalamide In acetone (40 ml) was dissolved N-(2-fluoro-4-chlorophenyl)-3,4,5,6-tetrahydroisophthalimide (2.8 g) and while stirring at room temperature, isopropylamine (0.6 g) was added. The mixture was allowed to stand for 10 hours, after which time the precipitate was recovered by filtration and washed with acetone. Yield 3.0 g.; m.p. 188°–189° C.

EXAMPLE 2

Production of N-allyl-N'-(2-fluoro-4-bromophenyl)-3,4,5,6-tetrahydrophthalamide In toluene (30 ml) was dissolved N-(2-fluoro-4-bromophenyl)-3,4,5,6-tetrahydroisophthalimide (2.0 g) and, while the solution was stirred at room temperature, a solution of allylamine (0.35 g) in toluene (10 ml) was added dropwise. The mixture was stirred for 90 minutes, after which time the precipitate was recovered by filtration and washed with toluene. Yield 2.3 g; m.p. 167°–169° C.

EXAMPLE 3

Production of N-benzyl-N'-(2-fluoro-4-chlorophenyl)-3,4,5,6-tetrahydrophthalamide In acetone (50 ml) was dissolved N-benzyl-3,4,5,6-tetrahydroisophthalimide (2.4 g), followed by addition of 2-fluoro-4-chloroaniline (1.5 g). The mixture was stirred at 40°–50° C. for 2 hours, after which time the precipitate was recovered by filtration and washed with acetone. Yield 3.0 g.; m.p. 121°–123° C.

EXAMPLES 4–49

The following compounds were obtained by the reactions carried out in the same manner as described in Examples 1 to 3.

| No. | X | R | m.p.(°C.) |
|---|---|---|---|
| 4 | Cl | $CH_3$ | 169–170 |
| 5 | Cl | $C_2H_5$ | 182–183.5 |
| 6 | Cl | $n-C_3H_7$ | 168–169 |
| 7 | Cl | $-CH_2CH=CH_2$ | 157–158 |
| 8 | Cl | $n-C_4H_9$ | 144–146 |
| 9 | Cl | $i-C_4H_9$ | 164 |
| 10 | Cl | $sec.-C_4H_9$ | 177–179 |
| 11 | Cl | $t-C_4H_9$ | 209–210 |
| 12 | Cl | $n-C_5H_{11}$ | 152.5–153.5 |
| 13 | Cl | $i-C_5H_{11}$ | 168–169 |
| 14 | Cl | $n-C_6H_{13}$ | 138–139 |
| 15 | Cl | $t-C_4H_9-\overset{CH_3}{\underset{\|}{CH}}-$ | 204–205 |
| 16 | Cl | $n-C_7H_{15}$ | 145–146 |
| 17 | Cl | $C_6H_{13}-\overset{CH_3}{\underset{\|}{CH}}-$ | 141–143 |
| 18 | Cl | $n-C_8H_{17}$ | 136–137 |
| 19 | Cl | $n-C_9H_{19}$ | 132–133 |
| 20 | Cl | $n-C_{11}H_{23}$ | 124–126 |
| 21 | Cl | $n-C_{12}H_{25}$ | 125–127 |
| 22 | Cl | $n-C_{14}H_{29}$ | 125–127 |
| 23 | Cl | $n-C_{16}H_{33}$ | 125–127 |
| 24 | Cl | $n-C_{18}H_{37}$ | 119–121 |
| 25 | Cl | $C_4H_9-\overset{C_2H_5}{\underset{\|}{CH}}-CH_2-$ | 114–117 |
| 26 | Cl | ⟨H⟩- | 197.5–199 |
| 27 | Cl | $C_6H_5-CH_2CH_2-$ | 153–155 |
| 28 | Cl | $C_6H_5-CH_2CH_2CH_2-$ | 137–139 |
| 29 | Cl | ▷- | 177–178 |
| 30 | Cl | $i-C_3H_7O-(CH_2)_3-$ | 115–117 |
| 31 | Br | $CH_3$ | 178–180 |
| 32 | Br | $C_2H_5$ | 188–189 |
| 33 | Br | $n-C_3H_7$ | 184–185 |
| 34 | Br | $i-C_3H_7$ | 196–198 |
| 35 | Br | $n-C_4H_9$ | 171–172 |
| 36 | Br | $i-C_4H_9$ | 178–179 |
| 37 | Br | $sec.-C_4H_9$ | 184–186 |
| 38 | Br | $tert.-C_4H_9$ | 210–211 |
| 39 | Br | $n-C_5H_{11}$ | 152–153.5 |
| 40 | Br | $i-C_5H_{11}$ | 164–165.5 |
| 41 | Br | $n-C_6H_{13}$ | 159–160 |
| 42 | Br | $n-C_7H_{15}$ | 155–156 |
| 43 | Br | $n-C_8H_{17}$ | 141–142 |
| 44 | Br | $C_4H_9-\overset{C_2H_5}{\underset{\|}{CH}}-CH_2-$ | 112.5–115 |
| 45 | Br | $n-C_{10}H_{21}$ | 131.5–132.5 |
| 46 | Br | $n-C_{12}H_{25}$ | 129 |
| 47 | Br | ⟨H⟩- | 213–215 |
| 48 | Br | $C_6H_5-CH_2-$ | 132.5–133.5 |
| 49 | Cl | $CH_3O-(CH_2)_3-$ | 111–113 |

EXAMPLE 50

Production of N-(2,4-dichlorobenzyl)-N'-(2-fluoro-4-chlorophenyl)-3,4,5,6-tetrahydrophthalamide In toluene (20 ml) was dissolved N-(2-fluoro-4-chlorophenyl)-3,4,5,6-tetrahydroisophthalimide (2.8 g) and, with stirring at room temperature, 2,4-dichlorobenzylamine (1.8 g) was added dropwise. The mixture was stirred for a further 30 minutes, after which the precipitate was recovered by filtration and washed with a small amount of diethyl ether. Yield 3.0 g; m.p. 165°–166° C.

EXAMPLE 51

Production of N-(2-propargyl)-N'-(2-fluoro-4-chloro-phenyl)-3,4,5,6-tetrahydrophthalamide In carbon tetrachloride (30 ml) was dissolved N-(2-fluoro-4-chlorophenyl)-3,4,5,6-tetrahydroisophthalimide (2.8 g) and, with stirring at room temperature, propargylamine (0.6 g) was added dropwise over a period of 5 minutes. The mixture was stirred for 30 minutes, after which the precipitate was recovered by filtration and washed with a small amount of diethyl ether. Yield 2.0 g, m.p. 167°–168° C.

EXAMPLE 52

Production of N-(3-hydroxypropyl)-N'-(2-fluoro-4-chlorophenyl)-3,4,5,6-tetrahydrophthalamide In carbon tetrachloride (30 ml) was dissolved N-(2-fluoro-4-chlorophenyl)-3,4,5,6-tetrahydroisophthalimide (2.8 g) and, with stirring at room temperature, 3-aminopropanol (0.8 g) was added. The mixture was stirred for one hour. The precipitate was recovered by filtration and recrystallized from dimethylformamide-ethanol. Yield 2.0 g.; m.p. 138° C.

EXAMPLE 53

Production of N-(4-methylbenzyl)-N'-(2-fluoro-4-bromophenyl)-3,4,5,6-tetrahydrophthalamide In carbon tetrachloride (50 ml) was dissolved N-(2-fluoro-4-bromophenyl)-3,4,5,6-tetrahydroisophthalimide (3.2 g) and, with stirring at room temperature, 4-methylbenzylamine (1.1 g) was added dropwise over a period of 5 minutes. The mixture was further stirred for 3 hours, at the end of which time the precipitate was recovered by filtration and washed with a small amount of diethyl ether. Yield 2.5 g; m.p. 167°–168° C.

EXAMPLE 54

Production of N-(2-fluoro-4-chlorophenyl)-3,4,5,6-tetrahydrophthalamide.

In acetone (100 ml) was dissolved N-(2-fluoro-4-chlorophenyl)-3,4,5,6-tetrahydroisophthalimide (22.5 g), and under cooling, 25% aqueous ammonia (5.8 g) was added dropwise over a period of about one minute, the temperature of the system being maintained below 25° C. The mixture was further stirred for 30 minutes, after which the precipitate was recovered by filtration and washed with a small amount of cold acetone. Yield 22.2 g; m.p. 150°–151° C.

EXAMPLE 55

Production of N-(2-ethoxycarbonylmethyl)-N'-(2-fluoro-4-chlorophenyl)-3,4,5,6-tetrahydrophthalamide In acetonitrile (60 ml) was dissolved N-(2-fluoro-4-chlorophenyl)-3,4,5,6-tetrahydroisophthalimide (2.8 g). The solution was cooled to 22° C., and with stirring at room temperature, ethyl aminoacetate hydrochloride (1.4 g) was added and, then, triethylamine (1.2 g) was added dropwise over a period of 5 minutes. The mixture was further stirred for one hour and, then, at 60° C. for 30 minutes. The insolubles were filtered off when hot and the filtrate was concentrated to dryness. The residue was dissolved in chloroform (150 ml), washed with water, dried and concentrated to dryness. The residue was recrystallized from acetonitrile-n-hexane. Yield 1.8 g.; m.p. 170°–170.5°.

EXAMPLE 56

Production of N-(2-carboxyethyl)-N'-(2-fluoro-4-chlorophenyl)-3,4,5,6-tetrahydrophthalamide In acetonitrile (50 ml) was dissolved N-(2-fluoro-4-chlorophenyl)-3,4,5,6-tetrahydroisophthalimide (5.6 g), followed by addition of $\beta$-alanine (1.8 g). The mixture was stirred at 60° C. for 7 hours. After cooling, the precipitate was recovered by filtration and washed with acetonitrile and, then, with water. Yield 2.1 g; m.p. 158°–159° C.

EXAMPLE 57

Production of N-(2-ethylthioethyl)-N'-(2-fluoro-4-chlorophenyl)-3,4,5,6-tetrahydrophthalamide In carbon tetrachloride (50 ml) was dissolved N-(2-fluoro-4-chlorophenyl)-3,4,5,6-tetrahydroisophthalimide (2.8 g), and with stirring at room temperature, 2-ethylthioethylamine (1.1 g) was added dropwise over a period of about 3 minutes. After the dropwise addition had been completed, the mixture was further stirred for one hour and the precipitate was recovered by filtration. Yield 3.2 g, m.p. 147°–148° C., as recrystallized from n-hexane-chloroform.

EXAMPLE 58

Production of N-(1,2-bisethoxycarbonylethyl)-N'-(2-fluoro-4-chlorophenyl)-3,4,5,6-tetrahydrophthalamide In acetonitrile (50 ml) was dissolved N-(2-fluoro-4-chlorophenyl)-3,4,5,6-tetrahydroisophthalimide (2.8 g), followed by the addition of diethyl aspartate hydrochloride (2.7 g). Under stirring at room temperature, triethylamine (1.2 g) was added dropwise. The mixture was stirred at room temperature for one hour and, then, at 55° C. for 2 hours. After cooling, the insolubles were filtered off. The filtrate was concentrated to dryness, the residue was dissolved in chloroform (150 ml) and the solution was washed twice with 40 ml portions of water and dried over anhydrous sodium sulfate. The chloroform was distilled off and the residue was recrystallized from diethyl ether-n-hexane. Yield 3.1 g; m.p. 109°–110° C.

EXAMPLE 59

Production of
N-(2-cyanoethyl)-N'-(2-fluoro-4-chlorophenyl)-3,4,5,6-tetrahydrophthalamide In carbon tetrachloride (100 ml) was dissolved N-(2-fluoro-4-chlorophenyl)-3,4,5,6-tetrahydroisophthalimide, followed by the addition of β-aminopropionitrile (0.7 g) with stirring at room temperature. The mixture was further stirred for 3 hours. The precipitate was recovered by filtration and recrystallized from ethyl acetate. Yield 2.6 g, m.p. 160°–161° C.

EXAMPLE 60

Production of
N-(2-bromoethyl)-N'-(2-fluoro-4-chlorophenyl)-3,4,5,6-tetrahydrophthalamide In acetonitrile (30 ml) was dissolved N-(2-fluoro-4-chlorophenyl)-3,4,5,6-tetrahydroisophthalimide (2.8 g), and with stirring at room temperature, 2-bromoethylamine hydrochloride (2.05 g) was added, followed by the dropwise addition of triethylamine (1.1 g). A further amount (10 ml) of acetonitrile was added and the mixture was stirred for 90 minutes, at the end of which time the precipitate was recovered by filtration. It was dissolved in chloroform (70 ml) and the small amounts of insolubles were filtered off. The filtrate was washed twice with 40 ml portions of water, dried over anhydrous sodium sulfate and concentrated to about one-half of the initial volume. To the concentrate was added n-hexane and, after cooling with ice, the precipitated crystals were collected by filtration. Yield 1.4 g.; m.p. 165°–166° C.

EXAMPLE 61

Production of
N-(3-acetyloxypropyl)-N'-(2-fluoro-4-chlorophenyl)-3,4,5,6-tetrahydrophthalamide In pyridine (20 ml) was dissolved N-(3-hydroxypropyl)N'-(2-fluoro-4-chlorophenyl)-3,4,5,6-tetrahydrophthalamide (1.5 g), followed by addition of acetic anhydride (10 ml). The mixture was stirred at room temperature for 30 minutes. The reaction mixture was poured into 200 ml of ice-water and, after stirring, the precipitate was recovered by filtration and rinsed with water. After drying, it was recrystallized from ethyl acetate-n-hexane. Yield 0.9 g; m.p. 127°–128° C.

EXAMPLE 62

Production of
N-(2-furfuryl)-N'-(2-fluoro-4-chlorophenyl)-3,4,5,6-tetrahydrophthalamide In acetonitrile (50 ml) was dissolved N-(2-fluoro-4-chlorophenyl)-3,4,5,6-tetrahydroisophthalimide (5.6 g), and with stirring at room temperature, a solution of furfurylamine (2.1 g) in acetonitrile (10 ml) was added dropwise. The mixture was stirred for 90 minutes, after which the precipitate was recovered by filtration and washed with a small amount of diethyl ether. Yield 6.3 g.; m.p. 149°–151° C.

EXAMPLE 63

Production of
N-(2-ethylsulfinylethyl)-N'-(2-fluoro-4-chlorophenyl)-3,4,5,6-tetrahydrophthalamide In chloroform (30 ml) was dissolved N-(2-ethylthioethyl)-N'-(2-fluoro-4-chlorophenyl)-3,4,5,6-tetrahydrophthalamide (1.9 g), and with stirring at a constant temperature of 3°–8° C. m-Chloroperbenzoic acid (1.0 g) was added in small portions over an hour. The mixture was stirred at the same temperature for 3 hours and, then, allowed to stand at room temperature overnight. The solution was washed twice with a 10% aqueous solution of sodium nitrite (20 ml each), washed with water and dried over anhydrous sodium sulfate. The chloroform layer was concentrated to dryness under reduced pressure and the residue was recrystallized from ethyl acetate. Yield 1.8 g; m.p. 136°–137° C.

EXAMPLE 64

Production of
N-(2-ethylsulfonylethyl)-N'-(2-fluoro-4-chlorophenyl)-3,4,5,6-tetrahydrophthalamide In chloroform (30 ml) was dissolved N-(2-ethylthioethyl)-N'-(2-fluoro-4-chlorophenyl)-3,4,5,6-tetrahydrophthalamide (1.9 g), and with stirring at room temperature, m-chloroperbenzoic acid (1.7 g) was added in small portions over a period of 5 minutes. The temperature of the solution rose to 47° C. temperarily. The solution was stirred at room temperature for 3 hours, at the end of which time it was cooled with ice and the precipitate was recovered by filtration and recrystallized from ethyl acetate. Yield 2.0 g.; m.p. 150°–151° C.

EXAMPLES 65–89

By procedures similar to those described in Examples 1 to 3 and 50 to 64, the following compounds were obtained.

| No. | X | R | m.p.(°C.) |
|---|---|---|---|
| 65 | Cl | 2-Cl-C$_6$H$_4$-CH$_2$- | 140–141 |
| 66 | Cl | 4-Cl-C$_6$H$_4$-CH$_2$- | 156–158 |
| 67 | Cl | 2,4-Cl$_2$-C$_6$H$_3$-CH$_2$- | 171–172 |
| 68 | Cl | 2-CH$_3$-C$_6$H$_4$-CH$_2$- | 154–156 |
| 69 | Cl | 3-CH$_3$-C$_6$H$_4$-CH$_2$- | 138–140 |
| 70 | Cl | 4-CH$_3$-C$_6$H$_4$-CH$_2$- | 153–154 |

-continued

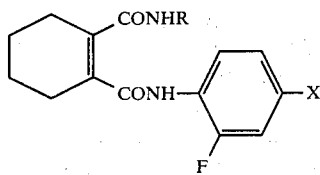

| No. | X | R | m.p.(°C.) |
|---|---|---|---|
| 71 | Cl | O$_2$N—⟨C$_6$H$_4$⟩—CH$_2$— | 184–185 |
| 72 | Cl | CH$_3$O—(CH$_2$)$_2$— | 131–132 |
| 73 | Cl | C$_2$H$_5$O—(CH$_2$)$_3$— | 118–119 |
| 74 | Cl | C$_2$H$_5$\\CHCH$_2$O—(CH$_2$)$_3$—/n-C$_4$H$_9$ | 108 |
| 75 | Br | CH$_3$-⟨C$_6$H$_4$⟩-CH$_2$— | 147–148 |
| 76 | Br | CH$_3$-⟨C$_6$H$_4$⟩-CH$_2$— | 168–169 |
| 77 | Br | Cl,Cl-⟨C$_6$H$_3$⟩-CH$_2$— | 155–157 |
| 78 | Br | CH$_3$O—(CH$_2$)$_2$— | 133–134 |
| 79 | Br | CH$_3$O—(CH$_2$)$_3$— | 141 |
| 80 | Br | i-C$_3$H$_7$O—(CH$_2$)$_3$— | 122–124 |
| 81 | Br | H | 173–175 |
| 82 | Cl | C$_2$H$_5$OOC—CH(i-C$_3$H$_7$)— | 128–129 |
| 83 | Cl | C$_2$H$_5$OOC—CH$_2$CH$_2$—CH(C$_2$H$_5$OOC)— | 129.5–130.5 |
| 84 | Cl | C$_2$H$_5$OOC—CH(CH$_2$C$_6$H$_5$)— | 138–139 |
| 85 | Cl | n-C$_3$H$_7$S—(CH$_2$)$_2$— | 140–141 |
| 86 | Cl | n-C$_4$H$_9$S—(CH$_2$)$_2$— | 124–125 |
| 87 | Cl | n-C$_3$H$_7$SOC$_2$H$_4$— | 121–122 |
| 88 | Cl | n-C$_3$H$_7$SO$_2$C$_2$H$_4$— | 154–155 |
| 89 | Cl | n-C$_4$H$_9$SO$_2$C$_2$H$_4$— | 133–134 |

EXAMPLE 90

A wettable powder product was prepared comprising a milled mixture of 30 weight % of N-isopropyl-N'-(2-fluoro-4-chlorophenyl)-3,4,5,6-tetrahydrophthalamide, 5 weight % of sodium ligninsulfonate, 5 weight % of polyethylene glycol ether (Nonipol 85®) and 60 weight % of clay.

EXAMPLE 91

A granular preparation product was prepared comprising, as kneaded with water and granulated, 10 weight % of N-octyl-N'-(2-fluoro-4-chlorophenyl)-3,4,5,6-tetrahydrophthalamide, 5 weight % of sodium ligninsulfonate and 85 weight % of bentonite.

EXAMPLE 92

An emulsifiable concentrate was prepared comprising 20 weight % of N-propyl-N'-(2-fluoro-4-bromophenyl)-3,4,5,6-tetrahydrophthalamide, 75 weight % of xylene and 5 weight % of polyethylene glycol ether (Nonipol 85®.)

EXAMPLE 93

Biscuit-fired pots, 9 cm across, were each filled with tilled land soil and, after sowing the pot with seeds of crabgrass *Digitaria adscendens* HENR., pigweed *Amaranthus retroflexus* L. and *Glycine max* Merrill (soybean), a layer, 0.5 cm thick, of cover soil was applied. Then, using a spray gun, the surface of the soil was evenly sprayed with a dilution of the emulsifiable concentrate containing various compounds represented by formula (I). The emulsifiable concentrate was diluted with 10 l of water to provide 4 g, 10 g or 40 g active component per are. After 21 days, the effects and injuries to the plants were investigated. The herbicidal effects are expressed according to the following index system.

| Index | Effect | % Inhibition (weed-killing) |
|---|---|---|
| 0 | No | 0% |
| 1 | Slight | 0.1–50% |
| 2 | Low | 50.1–70% |
| 3 | Moderate | 70.1–87.5% |
| 4 | High | 87.6–99.9% |
| 5 | Very high | 100% |

The injuries to soybean plants are expressed according to the following index system.

| Index | Degree of injury | % Injury |
|---|---|---|
| 0 | None | 0% |
| 1 | Slight | 0.1–12.5% |
| 2 | Low | 12.6–30.0% |
| 3 | Moderate | 30.1–50.0% |
| 4 | High | 50.1–99.9% |
| 5 | Very high | 100% |

The results are set forth in Table 1. (Compound numbered mean the compounds obtained in the respectively corresponding number of Examples.)

TABLE 1

| Compound No. | Amount, g/are | Digitaria adscendens HENR. | Amaranthus retroflexus L. | Glycine max Merrill |
|---|---|---|---|---|
| 1 | 4 | 5 | 5 | 0 |
|  | 40 | 5 | 5 | 1 |
| 2 | 4 | 5 | 5 | 0 |
|  | 40 | 5 | 5 | 1 |
| 3 | 4 | 5 | 5 | 0 |
|  | 40 | 5 | 5 | 0 |
| 4 | 4 | 5 | 5 | 0 |
|  | 40 | 5 | 5 | 4 |
| 5 | 4 | 5 | 5 | 1 |
|  | 40 | 5 | 5 | 1 |
| 6 | 4 | 5 | 5 | 1 |
|  | 40 | 5 | 5 | 2 |
| 7 | 4 | 5 | 5 | 0 |
|  | 40 | 5 | 5 | 2 |
| 8 | 4 | 5 | 5 | 1 |
|  | 40 | 5 | 5 | 3 |
| 9 | 4 | 5 | 5 | 1 |
|  | 40 | 5 | 5 | 1 |
| 10 | 4 | 5 | 5 | 1 |
|  | 40 | 5 | 5 | 1 |
| 11 | 4 | 3 | 1 | 1 |
|  | 40 | 4 | 5 | 1 |
| 12 | 4 | 5 | 5 | 1 |
|  | 40 | 5 | 5 | 1 |
| 13 | 4 | 5 | 5 | 1 |
|  | 40 | 5 | 5 | 1 |
| 14 | 4 | 5 | 5 | 1 |

TABLE 1-continued

| Compound No. | Amount, g/are | Digitaria adscendens HENR. | Amaranthus retroflexus L. | Glycine max Merrill |
|---|---|---|---|---|
|  | 40 | 5 | 5 | 2 |
| 15 | 4 | 4 | 3 | 0 |
|  | 40 | 5 | 5 | 0 |
| 16 | 4 | 5 | 5 | 0 |
|  | 40 | 5 | 5 | 0 |
| 17 | 4 | 4 | 5 | 0 |
|  | 40 | 5 | 5 | 1 |
| 18 | 4 | 5 | 5 | 0 |
|  | 40 | 5 | 5 | 3 |
| 19 | 4 | 5 | 5 | 1 |
|  | 40 | 5 | 5 | 1 |
| 20 | 4 | 5 | 4 | 0 |
|  | 40 | 5 | 5 | 1 |
| 21 | 4 | 5 | 4 | 0 |
|  | 40 | 5 | 5 | 0 |
| 22 | 4 | 1 | 1 | 1 |
|  | 40 | 5 | 5 | 1 |
| 23 | 4 | 2 | 1 | 1 |
|  | 40 | 5 | 4 | 1 |
| 24 | 4 | 1 | 1 | 1 |
|  | 40 | 4 | 5 | 1 |
| 25 | 4 | 5 | 5 | 0 |
|  | 40 | 5 | 5 | 1 |
| 26 | 4 | 5 | 2 | 1 |
|  | 40 | 5 | 5 | 1 |
| 27 | 4 | 5 | 5 | 0 |
|  | 40 | 5 | 5 | 0 |
| 28 | 4 | 5 | 5 | 1 |
|  | 40 | 5 | 5 | 1 |
| 30 | 4 | 5 | 5 | 1 |
|  | 40 | 5 | 5 | 1 |
| 31 | 4 | 5 | 5 | 1 |
|  | 40 | 5 | 5 | 1 |
| 32 | 4 | 5 | 5 | 0 |
|  | 40 | 5 | 5 | 1 |
| 33 | 4 | 5 | 5 | 0 |
|  | 40 | 5 | 5 | 0 |
| 34 | 4 | 5 | 5 | 1 |
|  | 40 | 5 | 5 | 1 |
| 35 | 4 | 5 | 5 | 0 |
|  | 40 | 5 | 5 | 0 |
| 36 | 4 | 5 | 5 | 0 |
|  | 40 | 5 | 5 | 0 |
| 37 | 4 | 5 | 5 | 0 |
|  | 40 | 5 | 5 | 1 |
| 38 | 4 | 3 | 3 | 0 |
|  | 40 | 4 | 4 | 2 |
| 39 | 4 | 5 | 5 | 0 |
|  | 40 | 5 | 5 | 1 |
| 40 | 4 | 5 | 5 | 0 |
|  | 40 | 5 | 5 | 0 |
| 41 | 4 | 5 | 5 | 0 |
|  | 40 | 5 | 5 | 2 |
| 42 | 4 | 5 | 5 | 1 |
|  | 40 | 5 | 5 | 1 |
| 43 | 4 | 5 | 5 | 1 |
|  | 40 | 5 | 5 | 1 |
| 44 | 4 | 5 | 5 | 1 |
|  | 40 | 5 | 5 | 3 |
| 45 | 4 | 4 | 4 | 0 |
|  | 40 | 5 | 5 | 1 |
| 46 | 4 | 2 | 2 | 0 |
|  | 40 | 4 | 4 | 0 |
| 47 | 4 | 4 | 4 | 0 |
|  | 40 | 5 | 5 | 1 |
| 48 | 4 | 5 | 5 | 0 |
|  | 40 | 5 | 5 | 0 |
| 49 | 4 | 5 | 5 | 1 |
|  | 40 | 5 | 5 | 2 |
| 50 | 10 | 4 | 5 | 0 |
|  | 40 | 5 | 5 | 0 |
| 51 | 10 | 5 | 5 | 0 |
|  | 40 | 5 | 5 | 1 |
| 53 | 10 | 4 | 5 | 0 |
|  | 40 | 5 | 5 | 0 |
| 55 | 10 | 5 | 5 | 0 |
|  | 40 | 5 | 5 | 1 |
| 56 | 10 | 5 | 5 | 0 |
|  | 40 | 5 | 5 | 1 |
| 57 | 10 | 5 | 5 | 0 |
|  | 40 | 5 | 5 | 1 |
| 58 | 10 | 5 | 5 | 0 |
|  | 40 | 5 | 5 | 1 |
| 59 | 10 | 5 | 5 | 0 |
|  | 40 | 5 | 5 | 1 |
| 60 | 10 | 5 | 5 | 0 |
|  | 40 | 5 | 5 | 1 |
| 61 | 10 | 5 | 5 | 0 |
|  | 40 | 5 | 5 | 1 |
| 63 | 10 | 5 | 5 | 0 |
|  | 40 | 5 | 5 | 1 |
| 64 | 10 | 5 | 5 | 0 |
|  | 40 | 5 | 5 | 1 |
| 65 | 10 | 5 | 5 | 0 |
|  | 40 | 5 | 5 | 0 |
| 66 | 10 | 5 | 5 | 0 |
|  | 40 | 5 | 5 | 0 |
| 67 | 10 | 5 | 5 | 0 |
|  | 40 | 5 | 5 | 0 |
| 68 | 10 | 4 | 4 | 0 |
|  | 40 | 5 | 5 | 0 |
| 69 | 10 | 5 | 5 | 0 |
|  | 40 | 5 | 5 | 0 |
| 70 | 10 | 5 | 5 | 0 |
|  | 40 | 5 | 5 | 0 |
| 73 | 10 | 5 | 5 | 0 |
|  | 40 | 5 | 5 | 1 |
| 74 | 10 | 5 | 5 | 0 |
|  | 40 | 5 | 5 | 1 |
| 75 | 10 | 4 | 5 | 0 |
|  | 40 | 5 | 5 | 0 |
| 76 | 10 | 4 | 5 | 0 |
|  | 40 | 5 | 5 | 0 |
| 77 | 10 | 4 | 5 | 0 |
|  | 40 | 4 | 5 | 0 |
| 82 | 10 | 5 | 5 | 0 |
|  | 40 | 5 | 5 | 1 |
| 83 | 10 | 5 | 5 | 0 |
|  | 40 | 5 | 5 | 1 |
| 84 | 10 | 5 | 5 | 0 |
|  | 40 | 5 | 5 | 1 |
| 85 | 10 | 5 | 5 | 0 |
|  | 40 | 5 | 5 | 1 |
| 86 | 10 | 5 | 5 | 0 |
|  | 40 | 5 | 5 | 1 |
| 87 | 10 | 5 | 5 | 0 |
|  | 40 | 5 | 5 | 1 |
| 88 | 10 | 5 | 5 | 0 |
|  | 40 | 5 | 5 | 1 |
| 89 | 10 | 5 | 5 | 0 |
|  | 40 | 5 | 5 | 1 |
| Control* | 40 | 0 | 2 | 0 |

*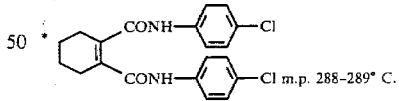 m.p. 288–289° C.

EXAMPLE 94

Plastic pots, 900 cm², were respectively filled with tilled land soil and sown with seeds of crabgrass *Digitaria adscendens* HENR., pigweed *Amaranthus retroflexus* L., lamb's quarters *Chenopodium album* L., inutade *Polygonum Blumei* Meisn., common purslane *Portulaca oleracea* L., maize *Zea Mays* L., soybean *Glycine Max* Merr. and cotton *Gossypium hirsutum* L. followed by the laying of cover soil in a thickness of 0.5 cm. Then, using a spray gun, the surface of the soil in each pot was evenly sprayed with an aqueous dilution of the emulsifiable concentrate containing the compound of general formula (I). Thus, said emulsifiable concentrate was diluted with 10 l of water to provide a concentration of 2.5 g., 5 g or 10 g of the active component [compound (I)] per are. After 30 days, the effects of each compound and the injuries caused thereby were investigated. The effects and injuries are scored and expressed in the same terms as those used in Example 93.

The results are shown in Table 2.

TABLE 2

| Compound No. | Amount, g/are | Digitaria adscendens HENR. | Amaranthus retroflexus L. | Chenopodium album L. | Polygonum Blumei Meisn. | Portulaca oleracea L. | Zea Mays L. | Glycine max Merrill | Gossypium hirsutum L. |
|---|---|---|---|---|---|---|---|---|---|
| 1 | 2.5 | 5 | 5 | 5 | 5 | 5 | 1 | 0 | 1 |
|   | 5 | 5 | 5 | 5 | 5 | 5 | 1 | 0 | 1 |
|   | 10 | 5 | 5 | 5 | 5 | 5 | 2 | 0 | 1 |
| 2 | 2.5 | 5 | 5 | 5 | 4 | 5 | 1 | 0 | 0 |
|   | 5 | 5 | 5 | 5 | 5 | 5 | 2 | 0 | 1 |
|   | 10 | 5 | 5 | 5 | 5 | 5 | 3 | 1 | 1 |
| 3 | 2.5 | 5 | 5 | 5 | 4 | 5 | 1 | 0 | 0 |
|   | 5 | 5 | 5 | 5 | 5 | 5 | 2 | 0 | 0 |
|   | 10 | 5 | 5 | 5 | 5 | 5 | 1 | 1 | 1 |
| 4 | 2.5 | 5 | 5 | 5 | 5 | 5 | 1 | 0 | 0 |
|   | 5 | 5 | 5 | 5 | 5 | 5 | 2 | 0 | 1 |
|   | 10 | 5 | 5 | 5 | 5 | 5 | 2 | 1 | 2 |
| 5 | 2.5 | 5 | 5 | 5 | 5 | 5 | 2 | 0 | 2 |
|   | 5 | 5 | 5 | 5 | 5 | 5 | 2 | 0 | 3 |
|   | 10 | 5 | 5 | 5 | 5 | 5 | 3 | 1 | 3 |
| 6 | 2.5 | 5 | 5 | 5 | 5 | 5 | 1 | 0 | 2 |
|   | 5 | 5 | 5 | 5 | 5 | 5 | 2 | 0 | 3 |
|   | 10 | 5 | 5 | 5 | 5 | 5 | 2 | 1 | 2 |
| 7 | 2.5 | 5 | 5 | 5 | 5 | 5 | 1 | 0 | 0 |
|   | 5 | 5 | 5 | 5 | 5 | 5 | 2 | 0 | 1 |
|   | 10 | 5 | 5 | 5 | 5 | 5 | 2 | 0 | 3 |
| 8 | 2.5 | 5 | 5 | 5 | 5 | 5 | 1 | 0 | 0 |
|   | 5 | 5 | 5 | 5 | 5 | 5 | 2 | 1 | 1 |
|   | 10 | 5 | 5 | 5 | 5 | 5 | 3 | 1 | 2 |
| 9 | 2.5 | 5 | 5 | 5 | 5 | 5 | 1 | 0 | 0 |
|   | 5 | 5 | 5 | 5 | 5 | 5 | 2 | 1 | 0 |
|   | 10 | 5 | 5 | 5 | 5 | 5 | 2 | 1 | 1 |
| 10 | 2.5 | 5 | 5 | 5 | 4 | 5 | 2 | 0 | 0 |
|   | 5 | 5 | 5 | 5 | 4 | 5 | 2 | 0 | 0 |
|   | 10 | 5 | 5 | 5 | 5 | 5 | 3 | 1 | 1 |
| 12 | 2.5 | 5 | 5 | 5 | 5 | 5 | 1 | 0 | 0 |
|   | 5 | 5 | 5 | 5 | 5 | 5 | 1 | 1 | 0 |
|   | 10 | 5 | 5 | 5 | 5 | 5 | 2 | 1 | 1 |
| 13 | 2.5 | 5 | 5 | 5 | 5 | 5 | 2 | 0 | 2 |
|   | 5 | 5 | 5 | 5 | 5 | 5 | 3 | 1 | 2 |
|   | 10 | 5 | 5 | 5 | 5 | 5 | 3 | 1 | 3 |
| 14 | 2.5 | 5 | 5 | 5 | 4 | 5 | 1 | 0 | 0 |
|   | 5 | 5 | 5 | 5 | 5 | 5 | 2 | 1 | 1 |
|   | 10 | 5 | 5 | 5 | 5 | 5 | 2 | 1 | 2 |
| 18 | 2.5 | 5 | 5 | 5 | 5 | 5 | 1 | 0 | 0 |
|   | 5 | 5 | 5 | 5 | 5 | 5 | 2 | 0 | 1 |
|   | 10 | 5 | 5 | 5 | 5 | 5 | 2 | 0 | 1 |
| 26 | 2.5 | 5 | 5 | 5 | 5 | 5 | 1 | 0 | 0 |
|   | 5 | 5 | 5 | 5 | 5 | 5 | 1 | 0 | 0 |
|   | 10 | 5 | 5 | 5 | 5 | 5 | 2 | 0 | 0 |
| 27 | 2.5 | 5 | 5 | 5 | 5 | 5 | 2 | 0 | 1 |
|   | 5 | 5 | 5 | 5 | 5 | 5 | 3 | 1 | 1 |
|   | 10 | 5 | 5 | 5 | 5 | 5 | 3 | 1 | 2 |
| 28 | 2.5 | 5 | 4 | 5 | 4 | 5 | 2 | 0 | 0 |
|   | 5 | 5 | 5 | 5 | 5 | 5 | 2 | 0 | 0 |
|   | 10 | 5 | 5 | 5 | 5 | 5 | 2 | 0 | 0 |
| 29 | 2.5 | 5 | 5 | 5 | 5 | 5 | 1 | 0 | 1 |
|   | 5 | 5 | 5 | 5 | 5 | 5 | 2 | 0 | 2 |
|   | 10 | 5 | 5 | 5 | 5 | 5 | 3 | 1 | 3 |
| 30 | 2.5 | 5 | 5 | 5 | 4 | 5 | 2 | 0 | 1 |
|   | 5 | 5 | 5 | 5 | 5 | 5 | 2 | 1 | 2 |
|   | 10 | 5 | 5 | 5 | 5 | 5 | 3 | 1 | 3 |
| 31 | 2.5 | 5 | 5 | 5 | 4 | 5 | 1 | 0 | 0 |
|   | 5 | 5 | 5 | 5 | 5 | 5 | 2 | 1 | 1 |
|   | 10 | 5 | 5 | 5 | 5 | 5 | 2 | 2 | 2 |
| 32 | 2.5 | 5 | 5 | 5 | 4 | 5 | 2 | 1 | 1 |
|   | 5 | 5 | 5 | 5 | 5 | 5 | 2 | 1 | 1 |
|   | 10 | 5 | 5 | 5 | 5 | 5 | 3 | 1 | 2 |
| 33 | 2.5 | 5 | 5 | 5 | 4 | 5 | 1 | 0 | 0 |
|   | 5 | 5 | 5 | 5 | 5 | 5 | 1 | 0 | 0 |
|   | 10 | 5 | 5 | 5 | 5 | 5 | 2 | 1 | 1 |
| 34 | 2.5 | 5 | 5 | 5 | 4 | 5 | 1 | 0 | 0 |
|   | 5 | 5 | 5 | 5 | 4 | 5 | 1 | 0 | 0 |
|   | 10 | 5 | 5 | 5 | 5 | 5 | 1 | 0 | 1 |
| 35 | 2.5 | 5 | 5 | 5 | 5 | 5 | 1 | 0 | 0 |
|   | 5 | 5 | 5 | 5 | 5 | 5 | 1 | 0 | 0 |
|   | 10 | 5 | 5 | 5 | 5 | 5 | 2 | 1 | 0 |
| 36 | 2.5 | 5 | 5 | 5 | 4 | 5 | 1 | 0 | 0 |

TABLE 2-continued

| Compound No. | Amount, g/are | Digitaria adscendens HENR. | Amaranthus retroflexus L. | Chenopodium album L. | Polygonum Blumei Meisn. | Portulaca oleracea L. | Zea Mays L. | Glycine max Merrill | Gossypium hirsutum L. |
|---|---|---|---|---|---|---|---|---|---|
|  | 5 | 5 | 5 | 5 | 4 | 5 | 1 | 0 | 0 |
|  | 10 | 5 | 5 | 5 | 5 | 5 | 2 | 0 | 0 |
| 37 | 2.5 | 5 | 5 | 5 | 4 | 5 | 1 | 0 | 0 |
|  | 5 | 5 | 5 | 5 | 4 | 5 | 1 | 0 | 0 |
|  | 10 | 5 | 5 | 5 | 5 | 5 | 1 | 0 | 0 |
| 39 | 2.5 | 5 | 5 | 5 | 4 | 5 | 1 | 0 | 0 |
|  | 5 | 5 | 5 | 5 | 4 | 5 | 1 | 0 | 0 |
|  | 10 | 5 | 5 | 5 | 5 | 5 | 2 | 0 | 0 |
| 40 | 2.5 | 5 | 5 | 5 | 4 | 5 | 0 | 0 | 0 |
|  | 5 | 5 | 5 | 5 | 5 | 5 | 1 | 0 | 0 |
|  | 10 | 5 | 5 | 5 | 5 | 5 | 1 | 0 | 0 |
| 41 | 2.5 | 5 | 5 | 5 | 4 | 5 | 0 | 0 | 0 |
|  | 5 | 5 | 5 | 5 | 4 | 5 | 1 | 0 | 0 |
|  | 10 | 5 | 5 | 5 | 5 | 5 | 1 | 0 | 0 |
| 42 | 2.5 | 5 | 5 | 5 | 4 | 5 | 0 | 0 | 0 |
|  | 5 | 5 | 5 | 5 | 4 | 5 | 1 | 0 | 0 |
|  | 10 | 5 | 5 | 5 | 5 | 5 | 1 | 0 | 0 |
| 43 | 2.5 | 5 | 5 | 5 | 4 | 5 | 1 | 0 | 0 |
|  | 5 | 5 | 5 | 5 | 5 | 5 | 2 | 0 | 0 |
|  | 10 | 5 | 5 | 5 | 5 | 5 | 2 | 1 | 0 |
| 47 | 2.5 | 5 | 5 | 5 | 4 | 5 | 2 | 0 | 0 |
|  | 5 | 5 | 5 | 5 | 4 | 5 | 2 | 0 | 0 |
|  | 10 | 5 | 5 | 5 | 4 | 5 | 2 | 0 | 1 |
| 52 | 2.5 | 5 | 5 | 5 | 4 | 5 | 2 | 1 | 1 |
|  | 5 | 5 | 5 | 5 | 5 | 5 | 2 | 1 | 2 |
|  | 10 | 5 | 5 | 5 | 5 | 5 | 2 | 1 | 2 |
| 62 | 2.5 | 5 | 5 | 5 | 5 | 4 | 0 | 0 | 0 |
|  | 5 | 5 | 5 | 5 | 5 | 5 | 1 | 0 | 0 |
|  | 10 | 5 | 5 | 5 | 5 | 5 | 2 | 0 | 1 |
| 65 | 2.5 | 4 | 5 | 4 | 2 | 5 | 0 | 0 | 0 |
|  | 5 | 5 | 5 | 5 | 3 | 5 | 0 | 0 | 0 |
|  | 10 | 5 | 5 | 5 | 5 | 5 | 0 | 0 | 0 |
| 67 | 2.5 | 4 | 5 | 4 | 4 | 5 | 0 | 0 | 0 |
|  | 5 | 5 | 5 | 5 | 4 | 5 | 0 | 0 | 0 |
|  | 10 | 5 | 5 | 5 | 4 | 5 | 1 | 0 | 0 |
| 70 | 2.5 | 4 | 5 | 4 | 2 | 5 | 0 | 0 | 0 |
|  | 5 | 5 | 5 | 4 | 3 | 5 | 0 | 0 | 0 |
|  | 10 | 5 | 5 | 5 | 4 | 5 | 1 | 0 | 0 |
| 71 | 2.5 | 5 | 5 | 5 | 4 | 5 | 0 | 0 | 0 |
|  | 5 | 5 | 5 | 5 | 5 | 5 | 1 | 0 | 0 |
|  | 10 | 5 | 5 | 5 | 5 | 5 | 0 | 0 | 0 |
| 72 | 2.5 | 5 | 5 | 5 | 5 | 5 | 1 | 0 | 0 |
|  | 5 | 5 | 5 | 5 | 5 | 5 | 2 | 0 | 0 |
|  | 10 | 5 | 5 | 5 | 5 | 5 | 3 | 1 | 2 |
| 78 | 2.5 | 5 | 5 | 5 | 5 | 5 | 0 | 0 | 0 |
|  | 5 | 5 | 5 | 5 | 5 | 5 | 1 | 1 | 0 |
|  | 10 | 5 | 5 | 5 | 5 | 5 | 1 | 1 | 0 |
| 79 | 2.5 | 2 | 4 | 4 | 5 | 4 | 0 | 0 | 0 |
|  | 5 | 5 | 5 | 5 | 5 | 5 | 1 | 0 | 0 |
|  | 10 | 5 | 5 | 5 | 5 | 5 | 2 | 1 | 1 |
| 80 | 2.5 | 4 | 4 | 5 | 5 | 5 | 0 | 0 | 0 |
|  | 5 | 4 | 5 | 5 | 5 | 5 | 0 | 0 | 0 |
|  | 10 | 5 | 5 | 5 | 5 | 5 | 1 | 1 | 0 |
| 81 | 2.5 | 5 | 5 | 5 | 5 | 5 | 1 | 0 | 0 |
|  | 5 | 5 | 5 | 5 | 5 | 5 | 2 | 0 | 1 |
|  | 10 | 5 | 5 | 5 | 5 | 5 | 3 | 1 | 2 |

What is claimed is:

1. A compound of the formula

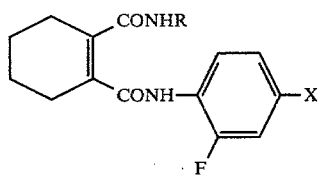

wherein X is chlorine or bromine, and R is:
(1) hydrogen;
(2) alkyl of 1–10 carbon atoms;
(3) a substituted straight-chain alkyl of 1 to 4 carbon atoms, the substituent being:
(a) hydroxyl,
(b) cyano,
(c) halogen,
(d) carboxyl,
(e) straight-chain or branched alkoxy of 1 to 8 carbon atoms,
(f) alkoxycarbonyl of 1 to 4 carbon atoms,
(g) carboxylic acyloxy of 1 to 10 carbon atoms,
(h) furyl which may be substituted by nitro, halogen or lower alkyl of 1 to 3 carbon atoms, or
(i) —$(O)_m SR^1$ in which $R^1$ is a straight-chain or branched alkyl of 1 to 5 carbon atoms and m is 0, 1 or 2;

(4) a cycloalkyl of 3 to 8 carbon atoms;
(5) a substituted C$_{3-8}$ cycloalkyl, the substituent being lower alkyl of 1 to 4 carbon atoms or halogen;
(6) an alkenyl of 2 to 8 carbon atoms; or
(7) an alkynyl of 2 to 8 carbon atoms.

2. A compound of the formula

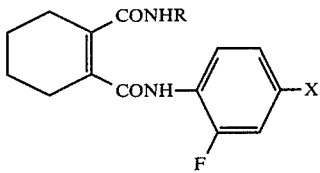

wherein X is chlorine or bromine, and R is hydrogen.

3. A compound of the formula

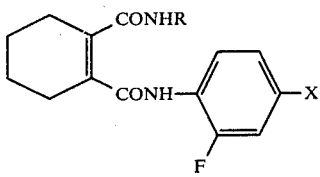

wherein X is chlorine or bromine, and R is alkyl of 1 to 10 atoms.

4. A compound of the formula

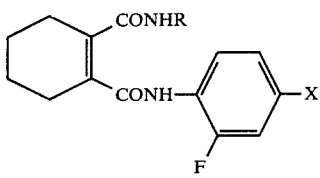

wherein X is chlorine or bromine, and R is a substituted straight-chain alkyl of 1 to 4 carbon atoms, the substituent being:
(a) hydroxyl,
(b) cyano,
(c) halogen,
(d) carboxyl,
(e) straight-chain or branched alkoxy of 1 to 8 carbon atoms,
(f) alkoxycarbonyl of 1 to 4 carbon atoms,
(g) carboxylic acyloxy of 1 to 10 carbon atoms,
(h) furyl which may be substituted by nitro, halogen or lower alkyl of 1 to 3 carbon atoms, or
(i) —(O)$_m$SR$^1$ in which R$^1$ is a straight-chain or branched alkyl of 1 to 5 carbon atoms and m is 0, 1 or 2.

5. A compound of the formula

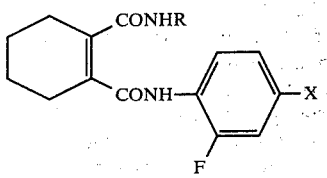

wherein X is chlorine or bromine, and R is cyclohexyl.

6. A compound of the formula

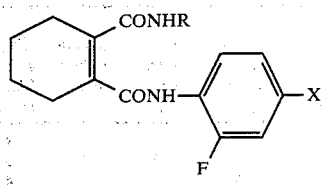

wherein X is chlorine or bromine, and R is allyl.

7. A compound of the formula

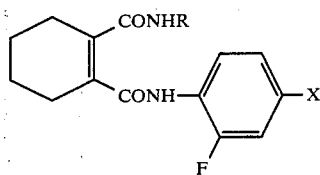

wherein X is chlorine or bromine, and R is propargyl.

8. A compound of the formula

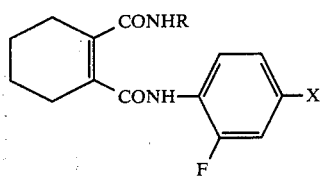

wherein X is chlorine or bromine, and R is C$_{1-10}$ alkyl, substituted by SR$^1$ in which R$^1$ is straight-chain or branched alkyl of 1 to 5 carbon atoms.

9. N-n-heptyl-N'-(2-fluoro-4-chlorophenyl)-3,4,5,6-tetrahydrophthalamide.

10. N-n-octyl-N'-(2-fluoro-4-chlorophenyl)-3,4,5,6-tetrahydrophthalamide.

11. N-n-butyl-N'-(2-fluoro-4-bromophenyl)-3,4,5,6-tetrahydrophthalamide.

12. A process for producing a compound of the formula:

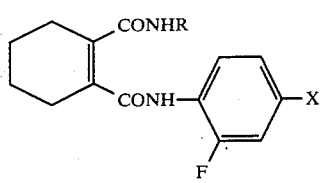

wherein X is chlorine or bromine, and R is hydrogen; alkyl of 1 to 10 carbon atoms; substituted C$_{1-10}$ alkyl, the substituent being hydroxyl, cyano, halogen, carboxyl, straight-chain or branched alkoxy of 1 to 8 carbon atoms, alkoxycarbonyl of 1 to 4 carbon atoms, carboxylic acyloxy of 1 to 10 carbon atoms, furyl which may be substituted by nitro, halogen or a lower alkyl of 1 to 3 carbon atoms, a group represented by the formula

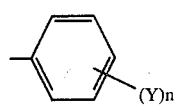

in which Y is hydrogen, halogen, lower alkyl, lower alkoxy, nitro or hydroxyl and n is an integer of 1, 2 or 3, or a group represented by the formula $R^1S(o)_m$—in which $R^1$ is straight-chain or branched alkyl of 1 to 5 carbon atoms and m is an integer of 0, 1 or 2; cycloalkyl of 3 to 8 carbon atoms; substituted $C_{3-8}$ cycloalkyl, the substituent being lower alkyl of 1 to 4 carbon atoms or halogen; alkenyl of 2 to 8 carbon atoms; or alkynyl of 2 to 8 carbon atoms; which comprises reacting a compound of the formula:

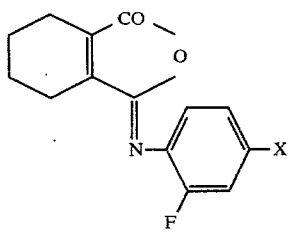

wherein X is as defined above, with a compound of the formula:

R—NH$_2$ wherein R is as defined above.

13. A process for producing a compound of the formula:

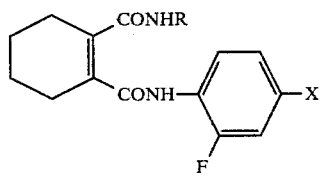

wherein X is chlorine or bromine, and R is alkyl of 1 to 10 carbon atoms; substituted $C_{1-10}$ alkyl, the substituent being hydroxyl, cyano, halogen, carboxyl, straight-chain or branched alkoxy of 1 to 8 carbon atoms, alkoxycarbonyl of 1 to 4 carbon atoms, carboxylic acyloxy of 1 to 10 carbon atoms, furyl which may be substituted by nitro, halogen or lower alkyl of 1 to 3 carbon atoms, represented by the formula

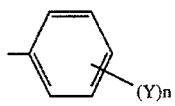

in which Y is hydrogen, halogen, lower alkyl, lower alkoxy, nitro or hydroxyl and n is integer of 1, 2 or 3, or represented by the formula $R^1S(o)_m$—in which $R^1$ is straight-chain or branched alkyl of 1 to 5 carbon atoms and m is integer of 0, 1 or 2; a cycloalkyl of 3 to 8 carbon atoms; substituted $C_{3-8}$ cycloalkyl, the substituent being lower alkyl of 1 to 4 carbon atoms or halogen; alkenyl of 2 to 8 carbon atoms; or alkynyl of 2 to 8 carbon atoms; which comprises reacting compound of the formula:

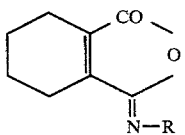

wherein R is as defined above, with amine of the formula

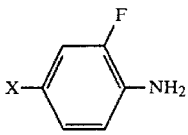

wherein X is as defined above.

* * * * *